United States Patent [19]

Fauconet et al.

[11] Patent Number: 5,705,688

[45] Date of Patent: Jan. 6, 1998

[54] PROCESS FOR THE PURIFICATION OF ACRYLIC ACID OBTAINED BY CATALYTIC OXIDATION OF PROPYLENE

[75] Inventors: Michel Fauconet, Valmont; Marc Esch, Freyming-Merlebach; Yves Samuel; Denis Laurent, both of Saint-Avold, all of France

[73] Assignee: Elf Atochem S.A., Puteaux, France

[21] Appl. No.: 682,188

[22] Filed: Jul. 17, 1996

[30] Foreign Application Priority Data

Jul. 18, 1995 [FR] France .................. 95 08672

[51] Int. Cl.$^6$ .................................................. C07C 51/42
[52] U.S. Cl. .................................................. 562/600
[58] Field of Search .................................................. 562/600

[56] References Cited

U.S. PATENT DOCUMENTS

| | | | |
|---|---|---|---|
| 3,555,082 | 1/1971 | Sennewald et al. | 562/532 |
| 3,658,886 | 4/1972 | Sennewald et al. | 562/208 |
| 3,689,541 | 9/1972 | Sennewald et al. | 562/600 |
| 3,868,417 | 2/1975 | Duembgen et al. | 562/600 |
| 3,932,500 | 1/1976 | Duembgen et al. | 562/600 |
| 4,166,774 | 9/1979 | Wagner | 203/82 |

Primary Examiner—Gary Geist
Assistant Examiner—Rosalynd A. Keys
Attorney, Agent, or Firm—Millen, White, Zelano, & Branigan, P.C.

[57] ABSTRACT

Acrylic acid obtained by catalytic oxidation of propylene, extracted by countercurrent washing of the reaction gases which at least one hydrophobic heavy solvent in an extraction column (C1) is purified. To this end, a distillation of the stream (5) obtained at the bottom of the column (C1) is conducted in a column (C3) so as to obtain a very pure acrylic acid stream (6) at the top of the column (C3), allowing acrylic acid to pass at the bottom (7); the bottom stream (7) is conveyed as feed into the lower part of a distillation column (C4) from which a stream (9) rich in maleic anhydride and impurities of boiling temperatures situated between that of acrylic acid and that of the heavy solvent is drawn off sideways on a tray situated between the feed and the top of the column; a stream (8) rich in acrylic acid, which is returned as feed to the column (C3) is distilled at the top of the column (C4); and a stream (1) containing heavy solvent and heavy impurities, which is recycled to the top of the column (C1), is recovered at the bottom of the column (C4).

16 Claims, 1 Drawing Sheet

PROCESS FOR THE PURIFICATION OF ACRYLIC ACID OBTAINED BY CATALYTIC OXIDATION OF PROPYLENE

The present invention relates to an improved process for the purification of acrylic acid.

The main route for the synthesis of acrylic acid which is employed industrially today is catalytic oxidation of propylene, which produces acrolein as intermediate. This reaction, which takes place in a gas phase, gives rise to a gas stream containing chiefly, besides acrylic acid, noncondensable gases: unconverted propylene, nitrogen, carbon monoxide and dioxide, "light"organic compounds, that is to say those while boiling point is lower than that of acrylic acid, water vapour, unconverted acrolein, impurities manufactured by side reactions, such as formaldehyde, acetic acid and the like and, finally, heavy compounds, that is to say those whose boiling point is higher than that of acrylic acid: maleic anhydride, furfuraldehyde, benzaldehyde and the like.

The processes for the purification of this reaction gas which are described in the literature consist in condensing this mixture and extracting the organic compounds by countercurrent washing with water or with heavy solvents.

The processes employing absorption by water have the disadvantage of extracting virtually all of the organic products present in the gas mixture in a relatively unselective manner. The purification of the aqueous solution thus formed requires difficult and costly separations by distillation and/or extraction.

French Patent No. 1 558 432 describes a process which consists in absorbing the organic compounds present in the reaction gas with the aid of esters of aliphatic or aromatic acids of high boiling points, or with tributyl or tricresyl phosphate. At the end of this absorption stage the light compounds (acrolein, formaldehyde) are removed at the top of a first distillation column, and a second distillation column makes it possible to obtain, at the top, and aqueous solution of acrylic acid which is more concentrated than in the prior art. However, the subsequent purification of the solution obtained, which still contains acetic acid and water, still requires costly separations.

The process described in French Patent No. 2 002 126 introduces an improvement by virtue of the use of a mixture of fractions of high boiling points, which is recovered at the bottom of the columns for purification of the esters manufactured from acrylic acid, containing chiefly maleates, polyacrylic acids and polyacrylates. This process makes it possible to clear in a single stage, at the top of a distillation column, most of the compounds of low boiling point, such as acrolein, formaldehyde, water and acetic acid. However, this process for the manufacture of acrylic esters if ill-suited to the production of pure acrylic acid, especially because of the presence, in the initial crude acrylic acid mixture, of the esterification derivatives recycled to the absorption stage.

An improvement is introduced in the process employing an extraction with the aid of a hydrophobic heavy solvent or of a mixture of hydrophobic heavy solvents, as described in French Patent No. 2 146 386 and German Patent No. 4 308 087, which makes it possible to obtain, at the end of the extraction stage, an anhydrous solution which is rid of a substantial proportion of the light organic products which constituted the initial gas mixture (acrolein, formaldehyde, acetic acid), thus appreciably facilitating the subsequent purification of acrylic acid. For greater clarity this column for the extraction of acrylic acid by absorption of the reaction gases with the aid of a heavy solvent or of a mixture of heavy solvents will be referred to as (c1).

According to this last process, the acrylic acid extracted, in solution in the heavy solvent or the mixture of heavy solvents, is, optionally, first of all freed from a proportion of the acetic acid and of the residual "light" compounds (that is to say all the impurities with a boiling point lower than acrylic acid) in a column (c2) and is then distilled in a column (c3).

However, it is very difficult to obtain a product which is completely free from heavy compounds (maleic anhydride, benzaldehyde, furfuraldehye, traces of solvent(s)) at the top of this column (c3) and, simultaneously, a mixture of heavy solvent(s) and of heavy compounds, free from residual acrylic acid, at the bottom of the column.

One is therefore constrained to choosing between two solutions, each of which has its disadvantages. If a minimum content of acrylic acid at the bottom is aimed at, the quality of the head stream is degraded, chiefly in respect of compound which are heavier than acrylic acid, and this makes it necessary to resort to a costly additional purification. Conversely, the search for an optimum quality of the acrylic acid distilled at the top of column (c3) means allowing acrylic acid to pass at the bottom. In this case, in the absence of a suitable process for recovering this acrylic acid in the bottom stream, as is the case, for example, within the scope of French patent application No. 2 146 386, this solution results in a costly loss in the recovery yield of acrylic acid.

In fact, in the French patent referred to, No. 2 146 386, the purpose of the stages which follow is to purify the heavy solvent or the mixture of heavy solvents in order to recycle it to the stage of the extraction of acrylic acid from the reaction gases (column c1). At the bottom of column (c3) a mixture is obtained composed of the heavy solvent or of the mixture of heavy solvents and of the heavier impurities from the process, namely:

- the "intermediate" impurities, that is to say those whose boiling point is between that of the heavy solvent and that of acrylic acid: maleic anhydride, furfuraldehyde, benzaldehyde and the like,
- the "heavy" impurities, that is to say those with a boiling point higher than that of the heavy solvent: esterified acrylic oligomers, polymers, polymerization inhibitors employed in the process, and the like.

At the end of this first distillation the impurities which are heavier than acrylic acid must be removed in order to avoid their accumulation during the recycling of the solvent or of the mixture of solvents to the extraction stage.

As described in the French patent referred to, No. 2 146 386, maleic anhydride can be removed in a column (c4) which may be either a distillation column (the impurity is withdrawn at the top of this column) or a column for extraction with water (the impurity is then purged at the bottom, in the aqueous stream).

In both cases the acrylic acid present at the bottom of column (c3) is lost, either at the top of the distillation column (c4) or in the water discharged from the washing column (c4). This gives rise to a considerable and costly loss in the recovery yield of acrylic acid.

Extraction with water has the additional disadvantage of giving rise to an aqueous stream which is rich in organic contamination, requiring a removal treatment that is costly in energy. In addition, the removal of the "intermediate" impurities other than maleic anhydride is insufficiently effective, and this results in an accumulation of these impurities in the solvent recycle loop. The consequence is then, unavoidably, the entrainment of these compounds into the distilled acrylic acid.

The removal of the "intermediate" impurities at the top of distillation column (c4) also has the disadvantage of entraining an appreciable loss of the heavy solvent(s) in this stream. Furthermore, the low water contents present at the bottom of the preceding column (c3) for purification of acrylic acid are concentrated at the top of this column for the removal of the "intermediate" products, and can result in an inconvenient phenomenon of precipitation of maleic acid produced by reaction of the anhydride form with water. In contrast to the anhydride, maleic acid is actually very poorly soluble in this mixture.

SUMMARY OF THE INVENTION

The Applicant has now developed a purification by distillation which avoids the above disadvantages. Surprisingly, it has, in fact, noticed that, in some conditions, it is possible to recover, in a fraction drawn off sideways in a distillation column (C4), a stream which is very rich in maleic anhydride and, at the top of this column, a stream which is very rich in acrylic acid, which can be recycled to the feed of the preceding column (C3) for purification of acrylic acid. As a result, it is possible to conduct the distillation in the column (C3) so as to obtain at the top of this column a stream which is very pure in respect of acrylic acid, practically free from heavy impurities, while accepting to allow to pass at the bottom a small proportion of the acrylic acid present in the feed. The acrylic acid present at the bottom of column (C3) is no longer lost, since it is recovered at the top of the next column (C4) for removal of the "intermediate" heavy products and can be recycled to the feed of the preceding column (C3). In addition, the stream drawn off sideways in this column (C4) is particularly concentrated in respect of "intermediate" heavy impurities (chiefly maleic anhydride, benzaldehyde and furfuraldehyde), and this makes it possible to avoid the accumulation of these impurities in the recycle loop, and the loss of heavy solvent(s) in this stream is greatly reduced.

BRIEF DESCRIPTION OF DRAWING

The attached drawing is a schematic flow sheet of a comprehensive embodiment of the invention.

The subject of the present invention is therefore a process for the purification of acrylic acid obtained by catalytic oxidation of propylene, extracted by countercurrent washing of the reaction gases with at least one hydrophobic heavy solvent in an extraction column (C1), characterized in that:

Figure 1:
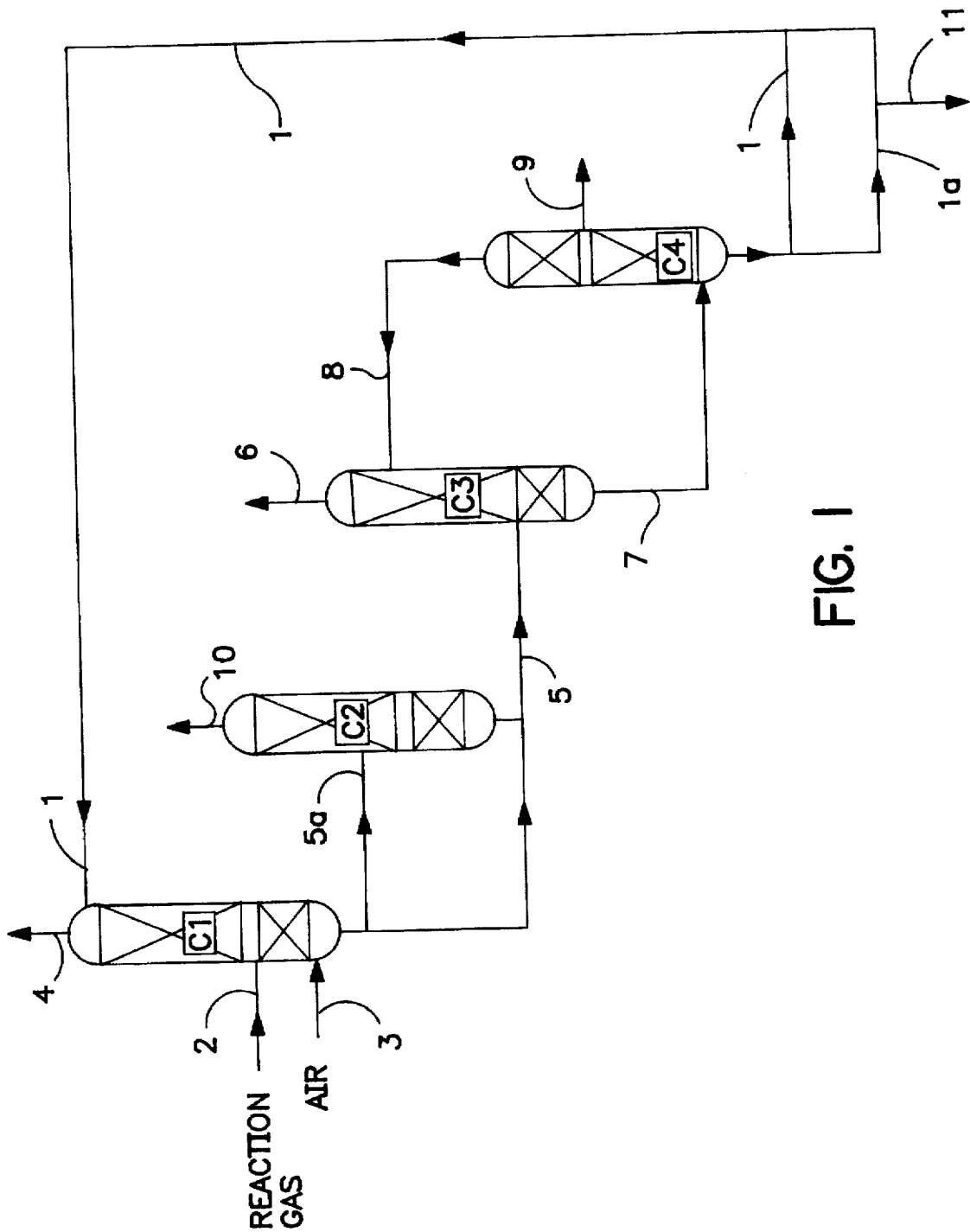

a distillation of the stream obtained at the bottom of the extraction column (C1), which contains the heavy extraction solvent(s), the required acrylic acid and impurities, chiefly impurities whose boiling temperatures are higher than that of acrylic acid, is conducted in a distillation column (C3), the said distillation being performed in conditions such that a stream which is very pure in respect of acrylic acid is obtained at the top of the said column (C3), allowing acrylic acid to pass at the bottom;

the stream from the bottom of the column (C3) is conveyed as feed into the lower part of a distillation column (C4) from which there is drawn off sideways, on a tray situated between the feed and the top of the column, a stream which is rich in maleic anhydride and impurities with boiling temperatures situated between that of acrylic acid and that of the said heavy solvent or of the lightest of the said heavy solvents employed as a mixture;

a stream rich in acrylic acid is distilled at the top of the column (C4); and a stream containing the said heavy solvent(s) and heavy impurities whose boiling temperatures are higher than that of the said heavy solvent or of the lightest of the said heavy solvents employed as a mixture is recovered at the bottom of the said column (C4), this stream being recycled to the top of the column (C1) for the extraction of the acrylic acid present in the reaction gases.

Before the stream obtained at the bottom of the column (C1) is introduced into the column (C3), the said stream can be advantageously freed from a proportion of its light residual impurities, such as acetic acid, at the top of a distillation column (C2).

In accordance with particular embodiments of the process according to the present invention:

the stream obtained at the bottom of the column (C1), if appropriate at the bottom of the column (C2), is conveyed onto a tray situated in the lower half of the column (C3) and the operating point of the said column (C3) is searched for so as to obtain:

at the top, a stream composed:

predominantly, that is at least 95% by weight of acrylic acid;

the remainder consisting of the heavy compounds: maleic anhydride, furfuraldehyde, benzaldehyde and traces of the heavy extraction solvent(s); and at the bottom, a stream composed:

predominantly, that is at least 95% by weight, of the heavy solvent(s) and of the heavy impurities;

the remainder consisting of acrylic acid;

the stream which rich in maleic anhydride and heavy impurities is drawn off sideways from the column (C4) on an intermediate tray situated above the feed between the lower quarter and the upper quarter of this column, at a temperature chosen so as to obtain a stream with a concentration of at least 20% by weight in respect of impurities with boiling temperatures between that of acrylic acid and that of the solvent or of the lightest of the solvents employed as a mixture;

the stream distilled at the top of the column (C4), which contains:

predominantly, that is at least 90% by weight, acrylic acid;

the remainder consisting of impurities of higher boiling temperatures;

is conveyed into the column (C3), at the main feed level of the is column or, advantageously , at a level situated above this feed; and before recycling the stream obtained at the bottom of column (C4) to the top of the column (C1), the said stream or a proportion of the said stream is freed from its heavy impurities with boiling temperatures higher than that of the solvent(s), for example by distillation techniques or extraction with the aid of a solvent, which are employed optionally as a supplement to a dissociation heat treatment optionally involving a catalyst.

In accordance with particular embodiments of the present invention:

the distillation in the column (C3) is conducted at a pressure of $2.66 \times 10^3$–$3.33 \times 10^4$ Pa (20–250 mm Hg), at a top temperature of 40°–120° C. and at a bottom temperature of 120°–230° C.;

the distillation in the column (C4) is conducted at a pressure of $2.66 \times 10^3$–$3.33 \times 10^4$ Pa (20–250 mm Hg), a a top temperature of 40°–120° C., at a bottom temperature of 120°–230° C. and at a side draw-off temperature of 40°–180° C.;

the distillation in the column (C2) is conducted at a pressure of $2.66 \times 10^3$–$3.33 \times 10^4$ Pa (20–250 mm Hg), at a top temperature to 30°–110° C. and at a bottom temperature of 70°–170° C.

The following points can also be specified:
(1) The distillation columns will be equipped preferably with the known devices for vacuum distillation of polymerizable products in the sections processing significant quantities of AA; perforated trays without downcomer are particularly recommended. The shells may be maintained by any suitable device at a temperature which is sufficient to avoid cold spots (which would bring about condensation of unstabilized product and thereby risks of polymerization).
(2) Polymerization inhibitors must be introduced into the distillation columns preferably in the presence of oxygen; the different inhibitors known for their effectiveness of inhibition of the polymerization of acrylic acid, such as phenoloic derviatives, phenothiazine and its derivaties, metal thiocarbamates, compounds containing nitroso groups, para-phenylenediamine derivatives and quinones may be suitable.
(3) In the above description the gas stream originating from (C1) may be partially recycled to the reaction zone. However, in all cases at least a proportion of this stream must be removed from the system; if this proportion must be discharged to the atmosphere, it must be purified either by catalytic oxidation or by passing through a combustion chamber.
(4) The stream leaving at the top of the column (C2), which is rich in acetic acid, may advantageously be introduced at a suitable point of the column (C1), which will make it possible to recover a considerable fraction of the acrylic acid present (and to remove the acetic acid).
(5) In the case where an inhibitor or a combination of light inhibitors is employed, the latter may be removed, at least partially, in the stream drawn off sideways from the column (C4).

The following examples illustrate the present invention without, however, limiting its cope. In these examples the percentages are given by weight. Distillation columns were employed which are installed according to the diagram in the single figure of the attached drawing and whose characteristics are indicated below. The feed to the columns may optionally be heated with the aid of an exchanger. An injection of oxygen is made into the columns. In the text relating to the description of the examples the trays of the columns are numbered starting from the top of the column (tray 0) down to the bottom of the column (tray n).

Column C1:
This column, 3 m in height and 38 mm in diameter, packed with "multiknit" type packing units, is fed:
  at the top, with a stream (1) of absorption solvent consisting of a mixture of 25% of diphenyl and 75% of disphenyl ether, pure or recovered at the bottom of column (C4), optionally after an operation of deconcentration of the impurities;
  in the first lower quarter, with the stream (2) of reaction gas from catalytic oxidation of propylene, precooled to 90° C.;
  at the bottom, with air (3) employed for carrying out stripping of the light compounds.

At the top of column (C1), a stream (4) is obtained, rich in light compounds (noncondensable gases, acrolein, formaldehyde, water and a proportion of acetic acid). At the bottom of column (C1) the recovered stream (5) forms a solution in the absorption solvent of acrylic acid with the residual acetic acid and the heavy constituents of this stream: maleic anhydride, furfuraldehyde, benzaldehyde, compounds of addition to acrylic acid and inhibitors.

Column C3:
This column, packed with "multiknit" type packing media, with an efficiency of 18 theoretical plates, is fed in the first lower third with a mixture characteristic of the stream (5) obtained at the bottom of column (C1). A proportion of the distillate (6) recovered at the top of the column after condensation is conveyed again to the top of the column to provide the reflux. In the lower portion the column is equipped with an electrically heated boiler.

Column C4:
This columns consists of 9 actual trays, with an efficiency of 5 theoretical plates, each tray being provided with orifices and an overflow. The feed, with a mixture characteristic of the stream (7) obtained at the bottom of column (C3), is preheated beforehand through an exchanger and then conveyed to the bottom of this column, at the level of the boiler with a thermal syphon heated by electrical resistances. A proportion of the distillate (8) recovered at the top of the column after condensation is conveyed again to the top of the column to provide the reflux. At the fifth tray level a system allows a proportion of the condensed liquid phase to be drawn off (at 9). This system is provided with a valve the opening of which is controlled automatically when the temperature measured on this tray reaches the fixed temperature set-point.

EXAMPLE 1

Into the distillation column (C3) operating at a pressure of 0.133 bar (100 mm Hg) are conveyed 1150 g/h of a stream (5) obtained at the bottom of extraction column (C1), including:
  90% of the heavy absorption solvent (mixture of 25% diphenyl and 75% diphenyl ether):
  9.31% of acrylic acid;
  0.07% of maleic anhydride.

At the top of column (C3) a proportion of the distilled stream (6) is returned so as to provide a reflux/draw-off ratio of 1/1. A mixture of acrylic acid containing 1.5% of hydroguinone, which acts at polymerization inhibitor, is also conveyed to the top of this column (C3), at a rate of 10 g/h. The temperature is varied at the boiler situated at the bottom of the column.

The results are summarized in the table below:

| Bottom temperature | 160° C. | 170° C. | 182° C. |
|---|---|---|---|
| % AA recovery | 89.3% | 94.3% | 99.8% |
| Top solvent (C3) | <0.001% | 0.02% | 0.112% |
| Top MAA (C3) | 0.006% | 0.212% | 0.529% |
| Bottom AA (C3) | 1.080% | 0.595% | 0.021% |

AA: acrylic acid
MAA: maleic anhydride

This example illustrates the difficulty of obtaining simultaneously acrylic acid of good quality, free from heavy compounds, at the top of column (C3), and a low acrylic acid content at the bottom (or a good recovery ratio at the top). Acrylic acid of a quality which is free from heavy compounds can be obtained only by accepting that a significant proportion of acrylic acid be allowed to pass at the bottom of the column.

· EXAMPLE 2

Into the bottom of column (C4), which operates at a pressure of 0.133 bar (100 mm Hg), are conveyed 1000 g/h of a mixture (7) recovered at the bottom of column (C3), including:

0.69% of acrylic acid;

0.06% of maleic anhydride;

0.005% of benzaldehyde;

0.003% of furfuraldehyde;

0.04% of hydroquinone;

the remainder consisting of the heavy absorption solvent (mixture of disphenyl and diphenyl ether) and of traces of heavy compounds of addition to the double bond of acrylic acid.

This mixture (7) is preheated to a temperature of 180° C. before being conveyed into the boiler of the column (C4). The temperature in the boiler is controlled at 182° C. The set-point temperature for drawing off the stream (9) which is rich in intermediate heavy compounds, at the fifth tray level, is set at 135° C. At the top of column (C4), at a temperature of 84° C., a stream (8) is distilled (6.4 g/h), consisting of:

97.1% of acrylic acid;

2.49% of maleic anhydride;

0.36% of benzaldehyde; and 0.07% of absorption solvent.

The stream (9) drawn off sideways at the fifth tray level (0.5 g/h) is composed of:

62% of maleic anhydride;

29% of heavy absorption solvent;

5.3% of acrylic acid;

3.1of benzaldehyde; and 1.2% of furfuraldehyde.

Finally, at the bottom of column (C4) a mixture (1) is drawn off, consisting essentially of the absorption heavy solvent and of the heavy compounds of addition to acrylic acid, as well as 0.2% of acrylic acid, 0.016% of maleic anhydride and 0.038% of hydroquinone.

In these conditions it can be seen that, if the stream (8) obtained at the top of column (C4) is returned to the feed of the preceding column (C3), the loss of acrylic acid is limited to the quantity of this acid which is drawn off sideways, that is lower than 0.5%. In the absence of the process which forms the subject of the present invention virtually all of the acrylic acid present in the feed to this column (C4) would be lost.

In addition, the process according to the invention allows the stream (1) of absorption solvent for recycling to be sufficiently deconcentrated in respect of intermediate impurities, so as to avoid the accumulation of these impurities in the loop. The reduction ratio of these impurities, which are drawn off sideways, is 48% in the case of maleic anhydride, 30% in the case of benzaldehyde and 20% in the case of furfuraldehyde.

EXAMPLE 3 (COMPARATIVE)

Into the bottom of column (C4), which operates at a pressure to 0.133 bar (100 mm Hg), are conveyed 1000 g/h of a stream preheated to 180° C., recovered at the bottom of the preceding column (C3), composed of:

1.6% of acrylic acid;

0.035% of maleic anhydride;

0.006% of benzaldehyde;

the remainder consisting of the absorption solvent (25% of diphenyl, 75% of diphenyl ether) and of the heavy compounds (derivates of addition to acrylic acid, inhibitors, etc).

The temperature at the bottom of the column is 182° C. In contrast to the preceding example, no stream is drawn off at an intermediate tray.

The distillate taken off at the top (16.6 g/h), at a temperature of 85° C., is composed of:

97.8% of acrylic acid;

1.41% of maleic anhydride;

0.22% of benzaldehyde; and 0.11% of absorption solvent.

The stream recovered at the bottom of column (C4) contains 0.047% of acrylic acid, 0.01% of maleic anhydride and 0.002% of benzaldehyde, the remainder consisting chiefly of the absorption solvent and the heavy compound of addition to acrylic acid and the inhibitors.

In these conditions the loss of acrylic acid in the stream recovered at the top of the column, in relation to the acrylic acid present in the steams leaving the column (C4), is 97%.

EXAMPLE 4

In this example the whole of the distillation loop (C1)–(C3)–(C4) is used successivley, with recycling of the products obtained during a previous pass over the distillation unit, namely of the solvent (1) recovered at the bottom of the column (C4) and the stream (8) distillate the top of column (C4), respectively as absorption solvent at the top of column C1 and as complement to the feed to the column (C3).

The column (C1) is fed:

at the top, with a mixture (1) of absorption solvent recovered at the bottom of column (C4) (2700 g/h), in which analysis finds low contents of acrylic acid (0.047%), of maleic anhydride (0.01%), of benzaldehyde (0.002%) and of hydroquinone (0.05%);

at the level of the first lower quarter, with the gases (2) from a catalytic oxidation reaction of propylene (2160 g/h), which are precooled to 90° C; and at the bottom (3), with air (600 l/h).

At the foot of this column (C1) a stream (5) is obtained, consisting of:

8.66% of acrylic acid;

0.064% of maleic anhdride;

0.006% of benzaldehyde;

0.005% of furfuraldehyde;

0.055% of hydroquinone;

the remainder consisting chiefly of the absorption solvent.

This mixture (5) is supplemented by the stream (8) obtained at the top of the column (C4) during a previous pass, composed of acrylic acid (97.8%), maleic anhydride (1.4%), benzaldehyde (0.22%), furfuraldehyde (0.12%) and solvent (0.11%). This mixture is conveyed (1231 g/h) as feed to column (C3) which operates at a pressure of 0.133 bar (100 mm Hg). The temperature at the boiler level is set at 165° C. At the top of column (C3) a proportion of the distilled stream (6) is returned so as to provide a reflux/draw-off ratio of ½. A mixture of acrylic acid containing 1.5% of hydroquinone is also conveyed to the top of this column, at a rate of 9.8 g/h. The product (6) which distills at the top at a temperature of 83° C. is essentially acrylic acid, additionally contains low contents of maleic anhydride (0.16%), benzaldehyde (0.01%) and furfuraldehyde (0.02%) and is free from absorption solvent.

The stream recovered at the bottom of the column (C3), which contains:

1.03% of acrylic acid;

(0.09% of maleic anhydride;

0.007% of benzaldehyde;

0.003% of furfuraldehyde;

0.073% of hydroquinone;

the remainder consisting of the absorption solvent and the heavy compounds of addition to acrylic acid, is conveyed (1000 g/h) to the bottom of column (C4) which operates at a pressure of 0.133 bar (100 mm Hg), at a temperature of 180° C. The temperature at the boiler level is controlled at 182° C. and the set point temperature for drawing off at the fifth tray level is set at 135° C. The product 8, distilled at the top of the column (9.3 g/h), intended to be returned as feed to column (C3), is composed of:

98% of acrylic acid;

1.45% of maleic anhydride;

0.17% of benzaldehyde;

0.15% of furfuraldehyde; and 0.08% of absorption solvent.

The stream 9 drawn off as side draw-off (1.31 g/h) contains:

12.94% of acrylic acid;

36.4% of maleic anhyride;

47.8% of absorption solvent 1.73% of benzaldehyde; and 0.83% of furfuraldehye.

Finally, the mixture (1) obtained at the bottom of column (C4), intended to be recycled to the top of column (C1), consists chiefly of the absorption solvent, of the heavy products of addition to acrylic acid and of hydroquinone (0.074%), with low contents of acrylic acid (0.04%) and maleic anhydride (0.02% ) and traces of benzaldehyde (0.002%) and of furfuraldehyde (content lower than 0.001%).

In these conditions the loss of acrylic acid in the side draw-off is only 1.6%, whereas the ratio of reduction in the intermediate impurities in the stream of absorption solvent to be recycled is 80% in the case of maleic anhydride and 79% in the case of benzaldehyde.

As already indicated, the stream 5 can be sent (along arrow 5a) to a distillation column (C2) in order to be freed (in 10) of its light residual impurities.

Before the stream 1 is recycled to the column (C1), it can also be freed (along arrow 1a) from its heavy impurities (in 11), by known techniques, such as those defined above.

We claim:

1. Process for the purification of acrylic acid obtained by catalytic oxidation of propylene, extracted by countercurrent washing of the reaction gases with at least one hydrophobic heavy solvent in an extraction column (C1), characterized in that:

a distillation of the stream (5) obtained at the bottom of the extraction column (C1), which contains the heavy extraction solvent(s), the required acrylic acid and impurities, chiefly impurities whose boiling temperatures are higher than that of acrylic acid, is conducted in a distillation column (C1), the said distillation being performed in conditions such that a stream (6) which is very pure in respect of acrylic acid is obtained at the top of the said column (C3), allowing acrylic acid to pass at the bottom (7);

the stream from the bottom (7) of the column (C3) is conveyed as feed into the lower part of a distillation column (C4) from which there is drawn off sideways, on a tray situated between the feed and the top of the column, a stream (9) which is rich in maleic anhydride and impurities with boiling temperatures situated between that of acrylic acid and that of the said heavy solvent or of the lightest of the said heavy solvents employed as a mixture;

a stream (8) rich in acrylic acid is distilled at the top of the column (C4); and a stream (1) containing the said heavy extraction solvent (s) and heavy impurities whose boiling temperatures are higher than that of the said heavy solvent or of the lightest of the said heavy solvents employed as a mixture is recovered at the bottom of the said column (C4), this stream being recycled to the top of the column (C1) for the extraction of the acrylic acid present in the reaction gases.

2. Process according to claim 1, characterized in that the stream (5) obtained at the bottom of the columns (C1) is freed from a proportion of its light residual impurities (10), such as acetic acid, at the top of a distillation column (C2).

3. Process according to claim 1, characterized in that the stream (5) obtained at the bottom of the column (C1), is appropriate at the bottom of the column (C2), is conveyed onto a tray situated in the lower half of the column (C3), and in that the operating point of the said column (C3) is searched for so as to obtain:

at the top, a stream (6) composed:
   predominantly, that is at least 95% by weight, of acrylic acid;
   the remainder consisting of the heavy compounds: maleic anhydride, furfuraldehyde, benzaldehyde and traces of the heavy extraction solvent(s); and at the bottom , a stream (7) composed:
   predominantly, that is at least 95% by weight, of the heavy solvent(s) and of the heavy impurities;
   the remainder consisting of acrylic acid.

4. Process according to claim 1, characterized in that the stream (9) which is rich in maleic anhydride and heavy impurities is drawn off sideways from the column (C4) on an intermediate tray situated above the feed between the lower quarter and the upper quarter of this column, at a temperature chosen so as to obtain a stream (9) with a concentration of at least 20% by weight in respect of impurities with boiling temperatures between that of acrylic acid and that of the extraction solvent or of the lightest of the solvents employed as a mixture.

5. Process according to claim 1, characterized in that the stream (8) distilled at the top of the column (C4), which contains:

predominantly, that is at least 90% by weight, acrylic acid,
   the remainder consisting of impurities of higher boiling temperatures, is conveyed into the column (C3), at the main feed level of this column or at a level situated above this feed.

6. Process according to claim 1, characterized in that, before recycling the stream (1) obtained at the bottom of column (C4) to the top of the column (C1), the said stream or a proportion of the said stream is freed (in 11) from its heavy impurities with boiling temperatures higher than that of the solvent(s), for example by distillation techniques or extraction with the aid of a solvent, which are employed optionally as a supplement to a dissociation heat treatment optionally involving a catalyst.

7. Process according to claim 1, characterized in that the distillation in the column (C3) is conducted at a pressure of $2.66 \times 10^3 - 3.33 \times 10^4$ Pa, at a top temperature of 40°–120° C. and at a bottom temperature of 120°–230° C.

8. Process according to claim 1, characterized in that the distillation in the column (C4) is conducted at a pressure of $2.66 \times 10^3 - 3.33 \times 10^4$ Pa, at a top temperature of 40°–120° C., at a bottom temperature of 120°–230° C. and at a side draw-off temperature of 40°–180° C.

9. Process according to claim 2, characterized in that the distillation in the column (C2) is conducted at a pressure of $2.66 \times 10^3$–$3.33 \times 10^4$ Pa, at a top temperature of 30°–110° C. and at a bottom temperature of 70°–170° C.

10. Process according to claim 2, characterized in that the stream (5) obtained at the bottom of the column (C1), if appropriate at the bottom of the column (C2), is conveyed onto a tray situated in the lower half of the column (C3), and in that the operating point of the said column (C3) is searched for so as to obtain:

at the top, a stream (6) composed:
   predominantly, that is at least 95% by weight, of acrylic acid;
the remainder consisting of the heavy compounds: maleic anhydride, furfuraldehyde, benzaldehyde and traces of the heavy extraction solvent(s); and at the bottom, a stream (7) composed:
   predominantly, that is at least 95% by weight, of the heavy solvent(s) and of the heavy impurities;
the remainder consisting of acrylic acid.

11. Process according to claim 10, characterized in that the stream (9) which is rich in maleic anhydride and heavy impurities is drawn off sideways from the column (C4) on an intermediate tray situated above the feed between the lower quarter and the upper quarter of this column, at a temperature chosen so as to obtain a stream (9) with a concentration of at least 20% by weight in respect of impurities with boiling temperature between that of acrylic acid and that of the extraction solvent or of the lightest of the solvents employed as a mixture.

12. Process according to claim 11, characterized in that the stream (8) distilled at the top of the column (C4), which contains:

predominantly, that is least 90% by weight, acrylic acid;
the remainder consisting of impurities of higher boiling temperatures, is conveyed into the column (C3), at the main feed level of this column or at a level situated above this feed.

13. Process according to claim 12, characterized in that, before recycling the stream (1) obtained at the bottom of column (C4) to the top of the column (C1), the said stream of a proportion of the said stream is is freed (in 11) from its heavy impurities with boiling temperatures higher than that of the solvent(s), for example by distillation techniques of extraction with the aid of a solvent, which are employed optionally as a supplement to a dissociation heat treatment optionally involving a catalyst.

14. Process according to claim 13, characterized in that the distillation in the column (C3) is conducted at a pressure of $2.66 \times 10^3$$3.33 \times 10^4$ Pa, at a top temperature of 40° 120° C. and a bottom temperature of 120°–230° C.

15. Process according to claim 14, characterized in that the distillation in the column (C4) is conducted at a pressure of $2.66 \times 10^3$–$3.33 \times 10^4$ Pa, at a top temperature of 40°–120° C., at a bottom temperature of 120° 230° C. and at a side draw-off temperature of 40°–180° C.

16. Process according to claim 15, characterized in that the distillation in the column (C2) is conducted at a pressure of $2.66 \times 10^3$–$3.33 \times 10^4$ Pa, at a top temperature of 30° 110° C. and a bottom temperature of 70° 170° C.

* * * * *